(12) United States Patent
Lee et al.

(10) Patent No.: US 8,696,576 B2
(45) Date of Patent: Apr. 15, 2014

(54) ULTRASOUND SYSTEM AND METHOD FOR PROVIDING CHANGE TREND IMAGE

(75) Inventors: Kwang Hee Lee, Seoul (KR); Dong Gyu Hyun, Seoul (KR)

(73) Assignee: Samsung Medison Co., Ltd., Gangwon-do (KR)

( * ) Notice: Subject to any disclaimer, the term of this patent is extended or adjusted under 35 U.S.C. 154(b) by 494 days.

(21) Appl. No.: 12/956,533

(22) Filed: Nov. 30, 2010

(65) Prior Publication Data

US 2011/0130661 A1 Jun. 2, 2011

(30) Foreign Application Priority Data

Nov. 30, 2009 (KR) .................. 10-2009-0116360

(51) Int. Cl.
*A61B 8/00* (2006.01)

(52) U.S. Cl.
USPC .......................................... 600/443; 600/438

(58) Field of Classification Search
None
See application file for complete search history.

(56) References Cited

U.S. PATENT DOCUMENTS

| 5,241,473 A | 8/1993 | Ishihara et al. |
| 5,743,266 A | 4/1998 | Levene et al. |
| 2002/0103437 A1 | 8/2002 | Jibiki |
| 2003/0055333 A1* | 3/2003 | Amemiya et al. ............ 600/437 |
| 2005/0070796 A1 | 3/2005 | Tsujita |
| 2007/0167763 A1* | 7/2007 | Hyun ............................ 600/437 |
| 2008/0221451 A1 | 9/2008 | Kanda |

FOREIGN PATENT DOCUMENTS

| EP | 1 884 195 A1 | 2/2008 |
| JP | 11-504242 | 4/1999 |
| JP | 2009-050389 | 3/2009 |
| KR | 10-2002-0064206 A | 8/2002 |
| WO | WO 96/33655 | 10/1996 |

OTHER PUBLICATIONS

Korean Office Action, issued in Korean Patent Application No. 10-2009-0116360, dated Dec. 28, 2011.
European Search Report issued in European Patent Application No. 10192778.8-2319, dated Mar. 25, 2011.

* cited by examiner

*Primary Examiner* — Unsu Jung
*Assistant Examiner* — Amanda Lauritzen Moher
(74) *Attorney, Agent, or Firm* — McDermott Will & Emery LLP

(57) ABSTRACT

There is disclosed an embodiment for providing a change trend image. An ultrasound data acquisition unit transmits ultrasound signal to a target object and receives echo signal reflected from the target object to sequentially acquire a plurality of ultrasound data. A processor is connected to the ultrasound data acquisition unit. The processor sequentially extracts feature values from the plurality of ultrasound data, allocates colors corresponding to each feature value and forms a change trend image with the colors indicative of a change trend of the extracted feature values over time.

14 Claims, 4 Drawing Sheets

FIG. 4

| | $U_1$ | $U_2$ | $U_3$ | $U_4$ | $U_5$ | $U_6$ | $U_7$ | $U_8$ |
|---|---|---|---|---|---|---|---|---|
| | | | | ULTRASOUND IMAGE | | | | |
| $I(P)$ | 20 | 10 | 10 | 10 | 30 | 200 | 200 | 190 |
| $I_{max}(P)$ | 20 | 20 | 20 | 20 | 30 | 200 | 200 | 200 |
| $M_{min}(P)$ | 1 | 1 | 1 | 1 | 5 | 6 | 6 | 6 |
| $NM_{min}(P)$ | 1 | $\frac{1}{2}$ | $\frac{1}{3}$ | $\frac{1}{4}$ | 1 | 1 | $\frac{1}{2}$ | $\frac{1}{3}$ |
| $\bar{I}(P)$ | 20 | 15 | 13.33 | 12.5 | 16 | 46.67 | 68.57 | 83.75 |

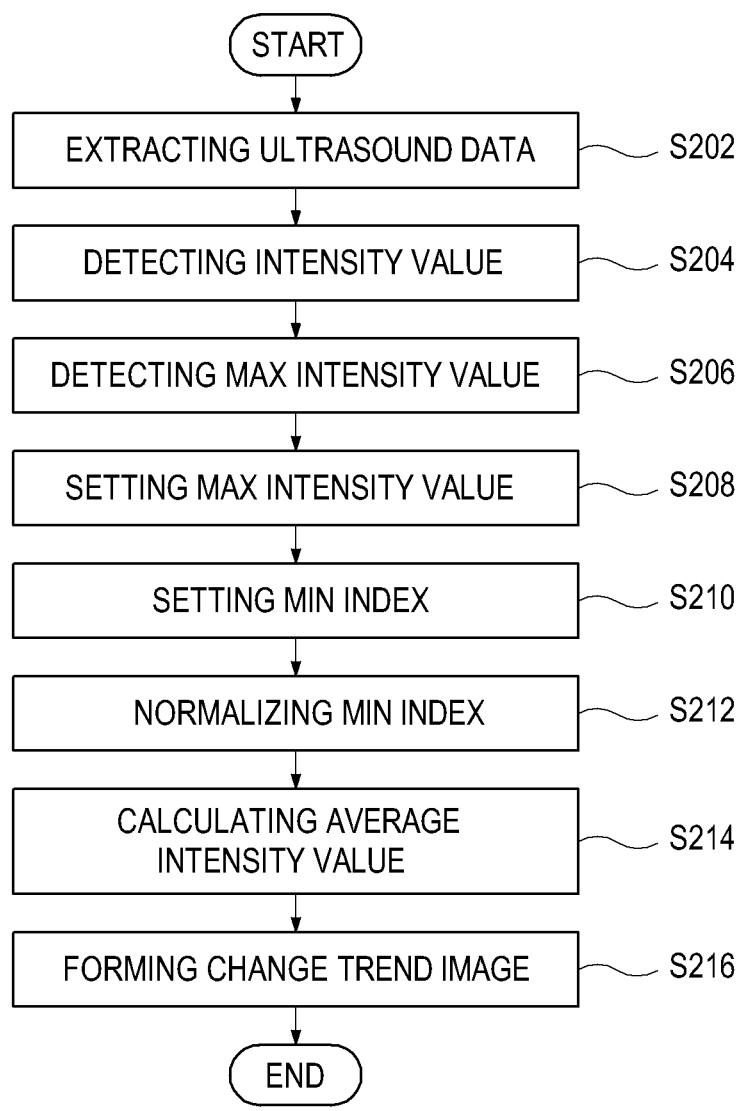

ULTRASOUND SYSTEM AND METHOD FOR PROVIDING CHANGE TREND IMAGE

CROSS-REFERENCE TO RELATED APPLICATIONS

The present application claims priority from Korean Patent Application No. 10-2009-0116360 filed on Nov. 30, 2009, the entire subject matter of which is incorporated herein by reference.

TECHNICAL FIELD

The present invention generally relates to ultrasound systems, and more particularly to an ultrasound system and method for providing a change trend image with colors.

BACKGROUND

An ultrasound system has become an important and popular diagnostic tool due to its non-invasive and non-destructive nature. The ultrasound system can provide high dimensional real-time ultrasound images of inner parts of target objects without a surgical operation.

The ultrasound system transmits ultrasound signals to the target objects, receives echo signals reflected from the target objects and provides ultrasound images of the target objects based on the echo signals. The ultrasound system may perform transmitting and receiving of ultrasound signals sequentially and iteratively to thereby form a plurality of ultrasound images.

The plurality of ultrasound images may be sequentially displayed on a display unit. Further, the ultrasound system may synthesize the plurality of ultrasound images to form a synthesis image for image enhancement. The synthesis image may also be displayed on the display unit. In such a case, since the ultrasound images and the synthesis image are sequentially displayed one by one on the display unit, it may be difficult to intuitively recognize the change of a specific feature such as a brightness change over time at a specific region in the ultrasound images.

SUMMARY

An embodiment for providing a change trend image is disclosed herein. In one embodiment, by way of non-limiting example, an ultrasound system includes: an ultrasound data acquisition unit configured to transmit ultrasound signal to a target object and receive echo signal reflected from the target object to sequentially acquire a plurality of ultrasound data; and a processor connected to the ultrasound data acquisition unit, the processor being configured to sequentially extract feature values from the plurality of ultrasound data, allocate colors corresponding to each feature value and form a change trend image with the colors indicative of a change trend of the extracted feature values over time.

In another embodiment, a method of providing a change trend image comprises: transmitting ultrasound signal to a target object and receiving echo signal reflected from the target object to sequentially acquire a plurality of ultrasound data; sequentially extracting feature values from the plurality of ultrasound data; allocating colors corresponding to each feature value; and forming a change trend image with the colors indicative of a change trend of the extracted feature values over time.

This Summary is provided to introduce a selection of concepts in a simplified form that are further described below in the Detailed Description. This Summary is not intended to identify key or essential features of the claimed subject matter, nor is it intended to be used in determining the scope of the claimed subject matter.

BRIEF DESCRIPTION OF THE DRAWINGS

FIG. 4 is a schematic diagram showing information on feature values from a plurality of ultrasound images including brightness values, maximum brightness values, minimum indexes, minimum index normalized values and average brightness values.

FIG. 5 is another flowchart showing a process of providing a change trend image showing a change trend on specific feature values extracted from ultrasound images over time.

DETAILED DESCRIPTION

This detailed description is provided with reference to the accompanying drawings. One of ordinary skill in the art may realize that the following description is illustrative only and is not in any way limiting. Other embodiments of the present invention may readily suggest themselves to such skilled persons having the benefit of this disclosure.

First Embodiment

Figure 1:
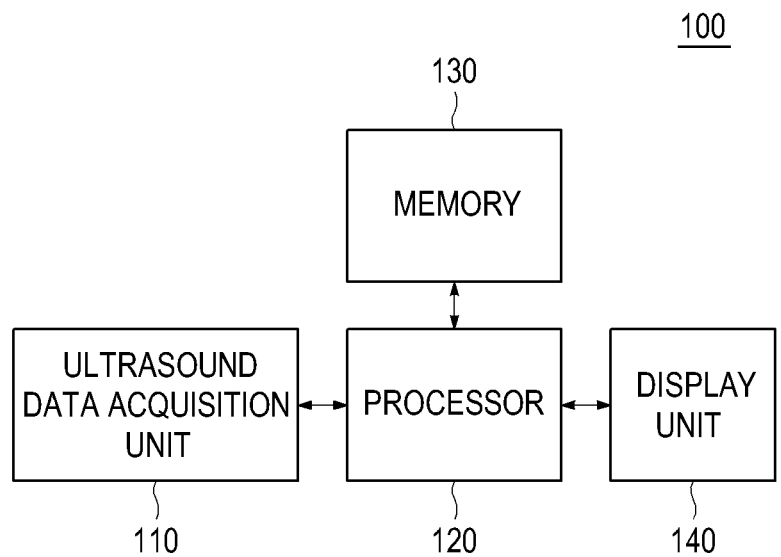
FIG. 1 is a block diagram showing an illustrative embodiment of an ultrasound system.

FIG. 1 is a block diagram showing an illustrative embodiment of an ultrasound system. As depicted therein, the ultrasound system 100 may include an ultrasound data acquisition unit 110, a processor 120, a memory 130 and a display unit 140.

The ultrasound data acquisition unit 110 may be configured to transmit and receive ultrasound signals to and from a target object to thereby output ultrasound data of the target object. The ultrasound data acquisition unit 110 may be explained more particularly by referring to FIG. 2.

Figure 2:
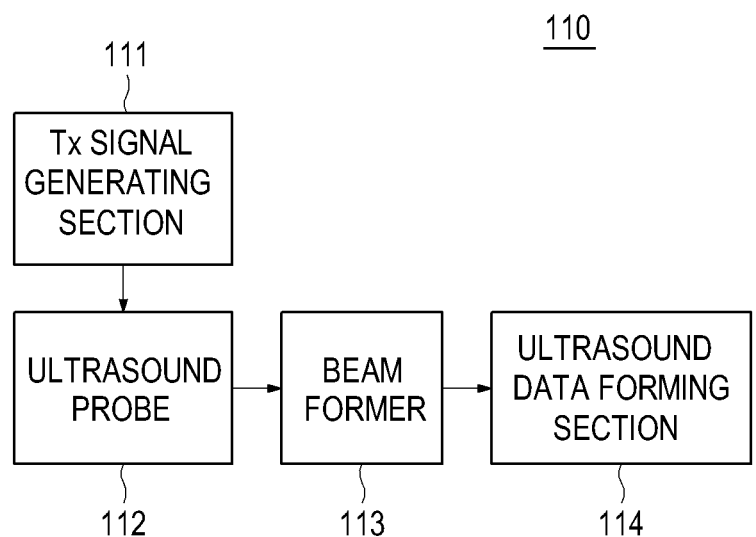
FIG. 2 is a block diagram showing an illustrative embodiment of an ultrasound data acquisition unit in FIG. 1.

FIG. 2 is a block diagram showing an illustrative embodiment of the ultrasound data acquisition unit 110. The ultrasound data acquisition unit 110 may include a transmit (Tx) signal generating section 111, an ultrasound probe 112 having a plurality of transducer elements (not shown), a beam former 113 and an ultrasound data forming section 114.

The Tx signal generating section 111 may be configured to generate Tx signals. The Tx signal generating section 111 may generate a plurality of Tx signals and apply delays to the Tx signals in consideration of distances between the respective transducer elements and focal points for acquiring ultrasound images indicative of the target object. The ultrasound images may include a brightness mode (B-mode) image, a Doppler mode (D-mode) image, a color mode (C-mode) image and a three-dimensional mode (3D mode) image. The B-mode image may represent a two-dimensional ultrasound image with brightness, which is determined according to reflection coefficients of the ultrasound signals reflected from the target object. The D-mode image may represent a Doppler spectrum image indicative of velocities of a moving target object, which may be measured over time by using the Doppler Effect. The C-mode image may represent an image showing velocities of moving object, which may be measured by using the Doppler Effect, with predetermined colors. The 3D mode image may represent a three-dimensional ultrasound image indicative of the target object, which may be formed by using reflection coefficients of the ultrasound signals reflected from the target object. The Tx signal generating section 111 may generate the Tx signals sequentially and iteratively.

The ultrasound probe 112 may include the plurality of transducer elements for reciprocally converting between ultrasound signals and electrical signals. The ultrasound probe 112 may be configured to transmit ultrasound signals to the target object in response to the Tx signals provided from the Tx signal generating section 111. The ultrasound probe 112 may further receive ultrasound echo signals reflected from the target object to thereby output the received signals. The received signals may be analog signals. The ultrasound probe 112 may form a plurality of received signals by transmitting and receiving ultrasound signals sequentially and iteratively to and from the target object based on the Tx signals. The ultrasound probe 112 may include a three-dimensional (3D) mechanical probe, a two-dimensional (2D) array probe and the like. However, it should be noted herein that the ultrasound probe 112 may not be limited thereto.

The beam former 113 may be configured to convert the received signals provided from the ultrasound probe 112 into digital signals. The beam former 113 may further apply delays to the digital signals in consideration of distances between the transducer elements and focal points to thereby output digital receive-focused signals. The receive-focusing and the delay application upon the plurality of received signals may be carried out sequentially and iteratively.

The ultrasound data forming section 114 may be configured to form ultrasound data corresponding to each of the plurality of ultrasound images based on the digital receive-focused signals provided from the beam former 113. The ultrasound data forming section 114 may form a plurality of ultrasound data sequentially and iteratively based on the plurality of digital receive-focused signals. The plurality of ultrasound data may be radio frequency (RF) data. However, it should be noted herein that the ultrasound data may not be limited thereto. The ultrasound data forming section 114 may further perform various signal processing (e.g., gain adjustment) upon the digital receive-focused signals.

Referring back to FIG. 1, the processor 120 is connected to the ultrasound data acquisition unit 110. The processor 120 may form a plurality of ultrasound images based on the plurality of ultrasound data sequentially provided from the ultrasound data acquisition unit 110. The processor 120 may extract specific feature values from the plurality of ultrasound images to obtain a change trend of the specific feature values over time. The specific feature values may include at least one of a maximum brightness value, a normalized value of minimum index, an average brightness value, a normalization function obtained by normalizing an accumulated function of brightness values, first index information on brightness values over a predetermined critical value, a dispersion of brightness values, a standard deviation of brightness values, a skewness of brightness values, a kurtosis of brightness values, a minimum brightness value, a brightness value of an $N^{th}$ ultrasound image, wherein N is a natural number, a orientation change function of a brightness value gradient and a phase change function of the brightness value gradient. For simplicity of the below description, it is considered that the feature values may include the maximum brightness value, the normalized value of minimum index and the average brightness value. However, the feature values are not limited thereto.

Furthermore, the processor 120 may form a change trend image showing the extracted feature values with colors over time.

Figure 3:
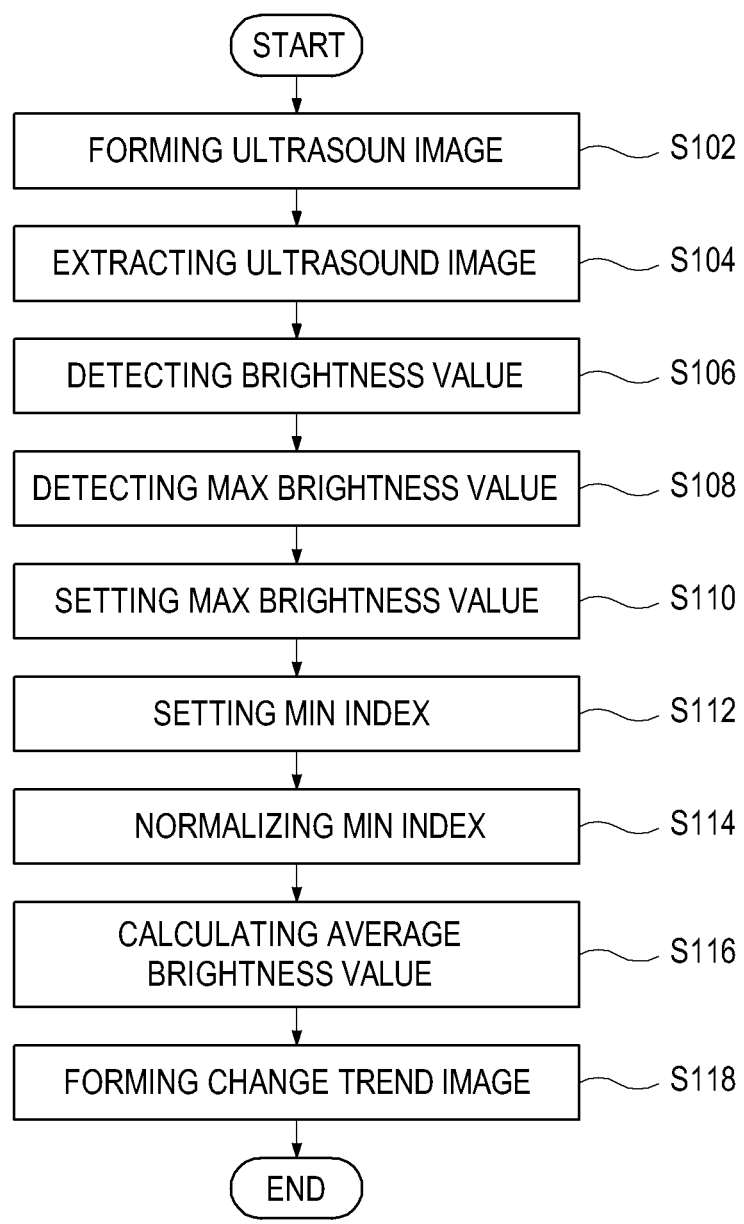
FIG. 3 is a flowchart showing a process of providing a change trend image showing a change trend on specific feature values extracted from ultrasound images over time.

FIG. 3 is a flowchart showing a process of forming a change trend image over time based on the extracted feature values. The processor 120 may form the ultrasound images including index information based on the ultrasound data provided from the ultrasound data acquisition section 110, at step S102. The index information may include information on a formation time of each of the ultrasound images or a serial number indicating a formation order of each of the ultrasound images. The processor 120 may sequentially and iteratively form a plurality of ultrasound images based on the ultrasound data sequentially provided from the ultrasound data acquisition section 110. The ultrasound images formed at the processor 120 are sequentially stored in the memory 130, as shown in FIG. 4.

FIG. 4 is a schematic diagram showing information on feature values from a plurality of ultrasound images including brightness values, maximum brightness values, minimum indexes, minimum index normalized values and average brightness values.

The processor 120 may extract the plurality of ultrasound images from the memory 130, at step S104. In one embodiment, the processor may extract the ultrasound images from the first stored ultrasound image $U_1$ to the lately stored ultrasound image $U_8$, as shown in FIG. 4.

The processor 120 may detect the brightness value (I(p)) of any position (p) of the ultrasound images, at step S106. In one embodiment, the processor 120 may detect the I(p) "20", "10", "10", "10", "30", "200", "200" and "190" at p in the ultrasound images $U_1$-U8, as shown in FIG. 4. The p may denote a position of an arbitrary pixel in the two-dimensional ultrasound image such as the B-mode ultrasound image, the D-mode ultrasound image and the C-mode ultrasound image, and denote a position of an arbitrary voxel in the three-dimensional ultrasound image such as the 3D mode ultrasound image.

The processor 120 may detect a maximum brightness value at the position "p" based on the detected brightness values, at step S108. Furthermore, the processor 120 may set the maximum brightness value at the position "p" by using the detected maximum brightness values, at step S110. In one embodiment, the processor 120 may set the maximum brightness value ($I_{max}(p)$) by using the following equation (1)

$$I_{max}(p)=\max(I(p,i)) \quad (1)$$

wherein "i" denotes the index information. Thus, the processor 120 may initially set "20," which is detected from the ultrasound image $U_1$ as the $I_{max}(p)$, as depicted in FIG. 5. The processor 120 may compare the maximum brightness value with the brightness value of the position "p" of the ultrasound image $U_2$ to check which one is bigger. Since the brightness value "20" of the position "p" of the ultrasound image $U_2$ is smaller than the $I_{max}(p)$, the processor 120 may set the brightness values "20" as the $I_{max}(p)$ for the ultrasound image $U_2$. In the same manner, the processor 120 may set the maximum brightness values "20", "20", "30", "200", "200", "200" as $I_{max}(p)$ of the position "p" of the respective ultrasound image $U_{3-8}$, as shown in FIG. 4.

The processor 120 may set the minimum index at the position "p" of the ultrasound images by using the detected maximum brightness value, at step S112. The minimum index may be the index corresponding to the ultrasound image with the maximum brightness value detected. In one embodiment, the processor 120 may set the minimum index ($M_{min}(p)$) by using the following equation (2)

$$M_{min}(p)=\min(\arg\max(I_{max}(p))) \quad (2)$$

In one embodiment, the processor 120 may initially set "1" as the minimum index since the brightness value at the position "p" of the ultrasound image $U_1$ is the maximum brightness value. Since the brightness value at the position "p" of the ultrasound image $U_1$ is set as the $I_{max}(p)$ of at the position "p" for the ultrasound images $U_2$-$U_4$, the processor 120 may set "1" as the minimum index at the position "p" of the ultrasound images $U_2$-$U_4$, as shown in FIG. 4. In the same manner, the processor 120 may set the minimum index at the position "p" of the ultrasound images $U_5$-$U_8$ to "5", "6", "6" and "6," as shown in FIG. 4.

The processor 120 may calculate a normalized value by normalizing the minimum index of the plurality of ultrasound images, at step S114. In one embodiment, the processor 120 may calculate the normalized value ($NM_{min}(p)$) by using the following equation (3).

$$NM_{min}(p) = \frac{M_{min}(p)}{a}, \quad 0 \le NM_{min}(p) \le 1 \quad (3)$$

wherein "a" denotes an accumulated number of the same minimum index.

In one embodiment, the processor 120 may initially normalize the minimum index "1" at the position "p" of the ultrasound image U1 by using the equation (3) to thereby obtain a normalizing value "1," as shown in FIG. 4. The processor 120 may calculate the normalizing value by normalizing the minimum index at the position "p" of the ultrasound image $U_2$ by using the equation (3) to thereby obtain a normalizing value "½." In the same manner, the processor 120 may calculate the normalizing values by normalizing the minimum indices at the position "p" in each of the ultrasound image $U_3$-$U_8$ to thereby obtain normalizing values "⅓," "¼," "1," "½" and "⅓," as shown in FIG. 4.

The processor 120 may calculate an average of brightness values at the position "p" from the sequentially formed ultrasound images, at step S116. In one embodiment, the processor 120 may calculate the average brightness value ($\bar{I}(p)$) by using the following equation (4)

$$\bar{I}(p) = \frac{1}{i}\sum_i I(p) \quad (4)$$

wherein "i" denotes the number of the ultrasound images.

In other words, the processor 120 may calculate the average brightness value at the position "p" from the ultrasound image $U_1$ to thereby obtain an average brightness value "20" at the position "p" of the ultrasound image $U_1$ by using the equation (4), as shown in FIG. 4. The processor 120 may calculate the average brightness value at the position "p" from the ultrasound image $U_1$-$U_2$ to thereby obtain an average brightness value "15." The processor 120 may calculate the average brightness value at the position "p" from the ultrasound images $U_1$-$U_3$ to thereby obtain an average brightness value "13.33." In the same manner, the processor 120 may calculate average brightness values at the position "p" from the ultrasound images $U_4$-$U_8$ to thereby obtain "12.5," "16," "46.67," "68.57" and "83.75," as shown in FIG. 4.

The processor 120 may form a change trend image by using the feature values such as the normalized value ($NM_{min}(p)$), the average brightness value ($\bar{I}(p)$) and the maximum brightness value ($I_{max}(p)$), at step S118. The processor 120 may allocate colors corresponding to each feature value. The change trend image may be formed by using various color models such as the HSV color model, the HSB color model, RGB color model, CMYK color model, Lab color model and the like.

In case of the HSV color model, the processor 120 may apply calculate channel values for a H channel, a S channel and a V channel by applying the normalized value, the maximum brightness value and the average brightness value to the following equation (5) to thereby form the change trend image.

$$H(p)=360 \times NM_{min}(p)$$

$$S(p)=\bar{I}(p)$$

$$V(p)=I_{max}(p) \quad (5)$$

wherein "H(p)" denotes the channel value of the H channel, "S(p)" denotes the channel value of the S channel and "V(p)" denotes the channel value of the V channel.

In this embodiment, the channel values of the H channel, the S channel and the V channel may be calculated by using the normalized value, the maximum brightness value and the average brightness value. However, the method of calculating the channel values of the H channel, the S channel and the V channel is not limited thereto. In another embodiment, at least one of channel values of the H channel, the S channel and the V channel may be calculated by using the normalized value, the maximum brightness value and the average brightness value, while another channel values of the H channel, the S channel and the V channel may be set as predetermined values.

The processor 120 may extract the colors relevant to a change trend of specific feature values from a color map to thereby form the change trend image. The color map may be formed relevant to the change trend.

The storage unit 130 may sequentially store the ultrasound images formed at the processor 120. The ultrasound images may include the index information. The display unit 140 may display the change trend image formed by the processor 120. Furthermore, the display unit 140 may display the ultrasound images formed by the processor 120. The display unit 140 may include a cathode ray tube (CRT) display, a liquid crystal display (LCD), organic light emitting diodes (OLED) display and the like.

Second Embodiment

FIG. 5 is another flowchart showing a change trend image forming process based on the extracted feature values over time.

The processor 120 may extract specific feature values from the plurality of ultrasound images to obtain a change trend of the specific feature values over time. The specific feature values may include at least one of a maximum intensity value, a normalized value of minimum index, an average intensity value, a normalization function obtained by normalizing an accumulated function of intensity values, first index information on intensity values over a predetermined critical value, a dispersion of intensity values, a standard deviation of intensity values, a skewness of intensity values, a kurtosis of intensity values, a minimum intensity value, a intensity value of an $N^{th}$ ultrasound image, wherein N is a natural number, a orientation change function of a intensity value gradient, and a phase change function of the intensity value gradient. For simplicity of the below description, it is considered that the feature values may include the maximum intensity value, the normalized value of minimum index and the average intensity value. However, the feature values are not limited thereto. Furthermore, the processor 120 may form a change trend image showing the extracted feature values with colors over time.

Referring to FIG. 5, the processor 120 may extract the plurality of ultrasound data from the memory 130, at step S202. In one embodiment, the processor 120 may extract the ultrasound data from the first stored ultrasound image to the lately stored ultrasound image.

The processor 120 may detect the intensity value based on the extracted ultrasound data, at step S204. In one embodiment, the processor 120 may detect a relevant ultrasound data at any position "p" of the ultrasound image by using a scan conversion relation between the ultrasound data and the ultrasound image to thereby detect the intensity value of the detected ultrasound data.

The processor 120 may detect the maximum intensity value at the position "p" by using the detected intensity value, at step S206. Furthermore, the processor 120 may set the maximum intensity value at the position "p" by using the detected maximum intensity value, at step S208. In the second embodiment, the method of detecting and setting the maximum intensity value is similar to the method of detecting and setting the maximum brightness value of the first embodiment. Thus, the detailed description of the method of detecting and setting the maximum intensity value is omitted.

The processor 120 may set the minimum index at the position "p" of the ultrasound image by using the detected maximum intensity value, at step S210. The minimum index may represent the index of the maximum intensity value detected ultrasound data. In the second embodiment, the method of setting the minimum index is similar to the method of the first embodiment. Thus, the detailed description of the method of setting the minimum index is omitted.

The processor 120 may calculate the normalized value by performing normalizing of the minimum index, at step S212. In the second embodiment, the method of calculating the normalized value of the minimum index is similar to the method of the first embodiment. Thus, the detailed description of the method of calculating the normalized value of the minimum index is omitted.

The processor 120 may calculate an average of intensity values at the position "p" from the sequentially formed ultrasound images relevant to the ultrasound data by using the intensity value, at step S214. In the second embodiment, the method of calculating the average intensity value is similar to the method of the first embodiment. Thus, the detailed description of the method of calculating the average intensity value is omitted.

The processor 120 may form the change trend image by using the detected change trend such as the normalized value, the average intensity value and maximum intensity value, at step S216.

The change trend image may be formed by using various color models such as the HSV color model, the HSB color model, RGB color model, CMYK color model, Lab color model and the like. The processor 120 may allocate colors corresponding to each feature value. The processor 120 may extract the colors relevant to the feature values from a color map to thereby form the change trend image. The color map may be formed relevant to the change trend.

Referring back to FIG. 1, the display unit 140 may display the change trend image formed by the processor 120.

Any reference in this specification to "one embodiment," "an embodiment," "example embodiment," "illustrative embodiment," etc. means that a particular feature, structure or characteristic described in connection with the embodiment is included in at least one embodiment of the present invention. The appearances of such phrases in various places in the specification are not necessarily all referring to the same embodiment. Further, when a particular feature, structure or characteristic is described in connection with any embodiment, it is submitted that it is within the purview of one skilled in the art to affect such feature, structure or characteristic in connection with other embodiments.

Although embodiments have been described with reference to a number of illustrative embodiments thereof, it should be understood that numerous other modifications and embodiments can be devised by those skilled in the art that will fall within the spirit and scope of the principles of this disclosure. More particularly, numerous variations and modifications are possible in the component parts and/or arrangements of the subject combination arrangement within the scope of the disclosure, the drawings and the appended claims. In addition to variations and modifications in the component parts and/or arrangements, alternative uses will also be apparent to those skilled in the art.

What is claimed is:

1. An ultrasound system, comprising:
   an ultrasound data acquisition unit having an ultrasound probe and configured to transmit an ultrasound signal to a target object and receive an echo signal reflected from the target object to sequentially and iteratively acquire a plurality of ultrasound data sets; and
   a processor connected to the ultrasound data acquisition unit, the processor being configured to form a plurality of ultrasound images including index information corresponding to a formation time of each of the ultrasound images, based on the sequentially acquired ultrasound data sets, sequentially extract feature values of a same position of the ultrasound images, allocate colors corresponding to each feature value and form a change trend image using a feature value from at least two ultrasound data sets with the colors indicative of a change trend of the extracted feature values over time.

2. The ultrasound system of claim 1, wherein the processor is configured to:
   detect brightness values of the same position of the plurality of ultrasound images;
   detect the change trend of the extracted feature based on the detected brightness values; and
   form the change trend image based on the detected change trend of the extracted feature.

3. The ultrasound system of claim 1,
   wherein the index information includes information on a serial number indicating a formation order of each of the ultrasound images.

4. The ultrasound system of claim 3, wherein the change trend of the extracted feature values includes at least one of a maximum brightness value, a normalized value of minimum index, an average brightness value, a normalized function obtained by normalizing an accumulated function of brightness values, first index information on brightness values over a predetermined critical value, a dispersion of brightness values, a standard deviation of brightness values, a skewness of brightness values, a kurtosis of brightness values, a minimum brightness value, a brightness value of an Nth ultrasound image, wherein N is a natural number, a orientation change function of a brightness value gradient, and a phase change function of the brightness value gradient.

5. The ultrasound system of claim 1, wherein the ultrasound data acquisition unit is further configured to:

form the plurality of ultrasound data including index information,
wherein the index information includes information on a formation time of each of the ultrasound images or a serial number indicating a formation order of each of the ultrasound images.

6. The ultrasound system of claim 5, wherein the processor is configured to:
   detect the intensity value of the plurality of ultrasound data;
   detect the change trend of the extracted feature based on the detected intensity value; and
   form the change trend image based on the detected change trend of the extracted feature.

7. The ultrasound system of claim 6, wherein the change trend of the extracted feature values includes at least one of a maximum intensity value, a normalized value of minimum index, an average intensity value, a normalized function obtained by normalizing an accumulated function of intensity values, first index information on intensity values over a predetermined critical value, a dispersion of intensity values, a standard deviation of intensity values, a skewness of intensity values, a kurtosis of intensity values, a minimum intensity value, an intensity value of an $N^{th}$ ultrasound image, wherein N is a natural number, a orientation change function of a intensity value gradient, and a phase change function of the intensity value gradient.

8. A method of providing a change trend image in an ultrasound system including an ultrasound data acquisition unit and a processor, the method comprising:
   transmitting, by the ultrasound data acquisition unit, an ultrasound signal to a target object and receiving an echo signal reflected from the target object to sequentially and iteratively acquire a plurality of ultrasound data sets;
   forming, by the processor, a plurality of ultrasound images including index information corresponding to a formation time of each of the ultrasound images, based on the sequentially acquired ultrasound data sets;
   sequentially extracting, by the processor, feature values of a same position of the ultrasound images;
   allocating, by the processor, colors corresponding to each feature value; and
   forming, by the processor, a change trend image using a feature value from at least two ultrasound data sets with the colors indicative of a change trend of the extracted feature values over time.

9. The method of claim 8, wherein extracting feature values comprises:
   detecting, by the processor, brightness values of the same positions of the plurality of ultrasound images; and
   detecting, by the processor, the change trend of the extracted feature values based on the detected brightness values.

10. The method of claim 8, wherein the index information includes information on a serial number indicating a formation order of each of the ultrasound images.

11. The method of claim 10, wherein the change trend of the extracted feature values includes at least one of a maximum brightness value, a normalized value of minimum index, an average brightness value, a normalized function obtained by normalizing an accumulated function of brightness values, first index information on brightness values over a predetermined critical value, a dispersion of brightness values, a standard deviation of brightness values, a skewness of brightness values, a kurtosis of brightness values, a minimum brightness value, a brightness value of an Nth ultrasound image, wherein N is a natural number, a orientation change function of a brightness value gradient, and a phase change function of the brightness value gradient.

12. The method of claim 8, wherein transmitting the ultrasound signal comprises:
   forming, by the processor, the plurality of ultrasound data including index information,
   wherein the index information includes information on a formation time of each of the ultrasound images or a serial number indicating a formation order of each of the ultrasound images.

13. The method of claim 12, wherein detecting change trend of the extracted feature comprises:
   detecting, by the processor, intensity values of the plurality of ultrasound data; and
   detecting, by the processor, the change trend of the extracted feature based on the detected intensity values.

14. The method of claim 13, wherein the change trend of the extracted feature values includes at least one of a maximum intensity value, a normalized value of minimum index, an average intensity value, a normalized function obtained by normalizing an accumulated function of intensity values, first index information on intensity values over a predetermined critical value, a dispersion of intensity values, a standard deviation of intensity values, a skewness of intensity values, a kurtosis of intensity values, a minimum intensity value, an intensity value of an $N^{th}$ ultrasound image, wherein N is a natural number, a orientation change function of a intensity value gradient, and a phase change function of the intensity value gradient.

* * * * *